(12) United States Patent
Millhouse et al.

(10) Patent No.: US 9,486,253 B2
(45) Date of Patent: Nov. 8, 2016

(54) LAMINOPLASTY FIXATION DEVICES

(71) Applicant: GLOBUS MEDICAL, INC., Audubon, PA (US)

(72) Inventors: Paul W. Millhouse, Wayne, PA (US); Michael L. Boyer, II, Phoenixville, PA (US); Christopher Angelucci, Schwenksville, PA (US); William E. Duffield, Collegeville, PA (US); Nirali Patel, Bristol, PA (US); Darren Clutter, East Greenville, PA (US); Noah Hansell, King of Prussia, PA (US)

(73) Assignee: Globus Medical, Inc., Audubon, PA (US)

( * ) Notice: Subject to any disclaimer, the term of this patent is extended or adjusted under 35 U.S.C. 154(b) by 48 days.

(21) Appl. No.: 14/554,210

(22) Filed: Nov. 26, 2014

(65) Prior Publication Data
US 2015/0080950 A1 Mar. 19, 2015

Related U.S. Application Data

(62) Division of application No. 11/936,334, filed on Nov. 7, 2007, now Pat. No. 8,926,664.

(60) Provisional application No. 60/864,731, filed on Nov. 7, 2006.

(51) Int. Cl.
*A61B 17/70* (2006.01)
*A61B 17/80* (2006.01)
*A61B 17/88* (2006.01)

(52) U.S. Cl.
CPC ......... *A61B 17/7071* (2013.01); *A61B 17/808* (2013.01); *A61B 17/8866* (2013.01)

(58) Field of Classification Search
CPC .................................................. A61B 17/7071
See application file for complete search history.

(56) References Cited

U.S. PATENT DOCUMENTS

| | | | |
|---|---|---|---|
| 3,971,384 A | 7/1976 | Hasson | |
| 5,672,177 A | 9/1997 | Seldin | |
| 5,827,286 A | 10/1998 | Incavo et al. | |
| 6,051,007 A | 4/2000 | Hogendijk et al. | |
| 6,066,175 A | 5/2000 | Henderson et al. | |
| 6,080,157 A | 6/2000 | Cathro et al. | |
| 6,235,059 B1 | 5/2001 | Renezech et al. | |
| 6,402,751 B1 | 6/2002 | Hoeck et al. | |
| 6,572,619 B2 | 6/2003 | Santilli | |
| 6,635,087 B2 | 10/2003 | Angelucci et al. | |
| 6,660,007 B2 | 12/2003 | Khanna | |
| 6,852,113 B2 | 2/2005 | Nathanson et al. | |
| 7,033,377 B2 | 4/2006 | Miller | |
| 7,112,222 B2 | 9/2006 | Fraser et al. | |
| 2002/0120335 A1 | 8/2002 | Angelucci et al. | |
| 2004/0030388 A1 | 2/2004 | Null et al. | |
| 2005/0085816 A1 | 4/2005 | Michelson | |
| 2005/0177160 A1 | 8/2005 | Baynham et al. | |
| 2005/0234456 A1 | 10/2005 | Malandain | |

(Continued)

*Primary Examiner* — Ellen C Hammond

(57) ABSTRACT

Devices and methods for treating degenerative conditions of the spine or for alleviating pain or discomfort associated with the spinal column are disclosed. In particular, laminoplasty fixation devices and methods are disclosed. Also disclosed, is a vertebral implant comprising a first bone engaging portion configured for securing to a first cut portion of a vertebra and a second bone engaging portion configured for securing to a second cut portion of the vertebra. A body portion is provided for associating the first and second bone engaging portions at a preselected spacing from each other, wherein the implant is adjustable to select said spacing.

17 Claims, 12 Drawing Sheets

(56) References Cited

U.S. PATENT DOCUMENTS

| | | |
|---|---|---|
| 2005/0251138 A1 | 11/2005 | Boris et al. |
| 2005/0273100 A1 | 12/2005 | Taylor |
| 2010/0057127 A1 | 3/2010 | McGuire et al. |
| 2011/0106083 A1 | 5/2011 | Voellmicke et al. |
| 2011/0106087 A1 | 5/2011 | Gamache |
| 2011/0106169 A1 | 5/2011 | Zalenski et al. |
| 2012/0165942 A1 | 6/2012 | Khanna |
| 2013/0060283 A1 | 3/2013 | Suh et al. |
| 2013/0197641 A1 | 8/2013 | Shepard et al. |
| 2013/0211524 A1 | 8/2013 | Hugues |
| 2013/0226249 A1 | 8/2013 | Konieczynski et al. |
| 2013/0231705 A1 | 9/2013 | Zalenski et al. |
| 2013/0261623 A1 | 10/2013 | Voellmicke et al. |
| 2014/0088648 A1 | 3/2014 | Chind |
| 2014/0114361 A1 | 4/2014 | Robinson |
| 2014/0135845 A1 | 5/2014 | Null et al. |

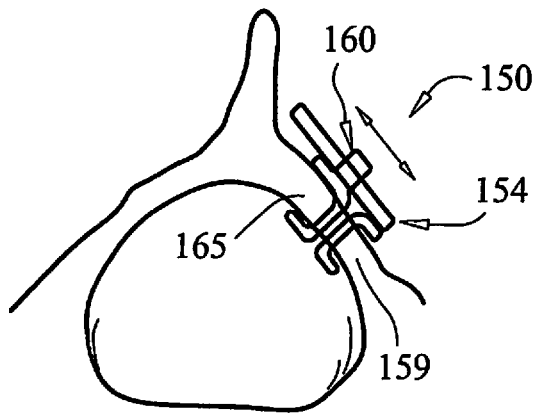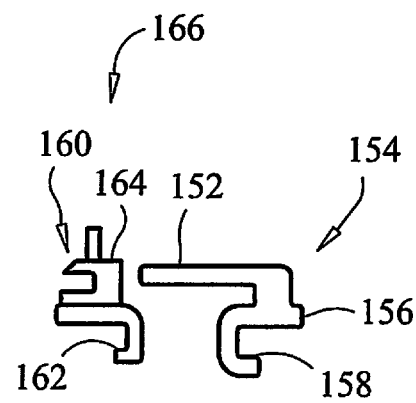
Fig. 13  Fig. 13A
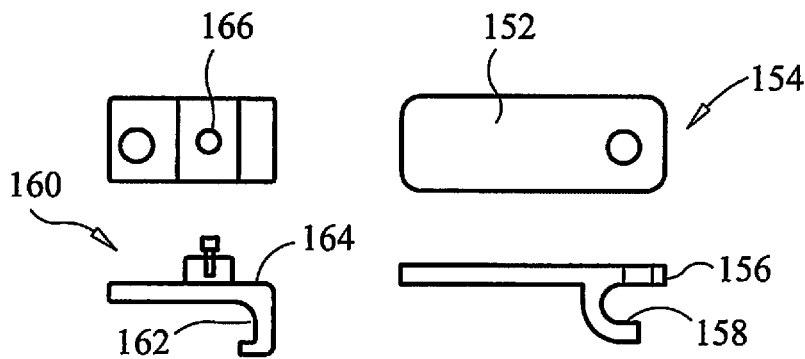
Fig. 14
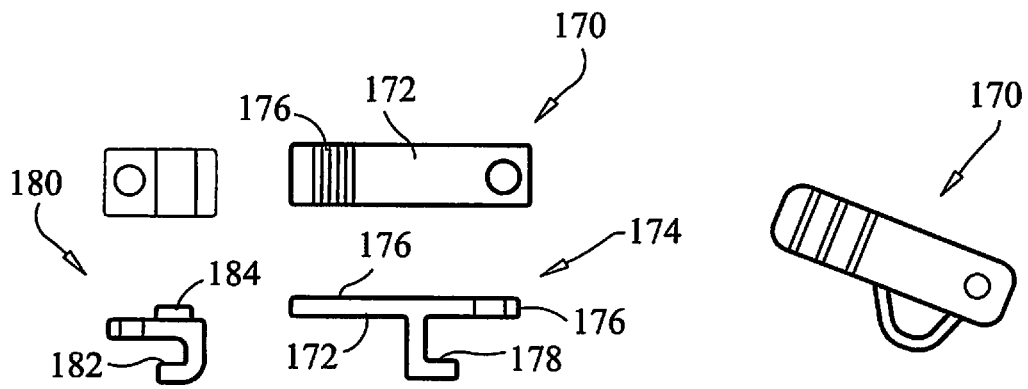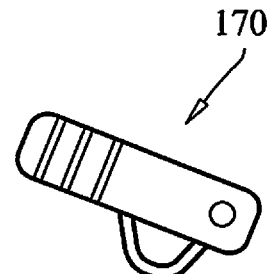
Fig. 15  Fig. 16

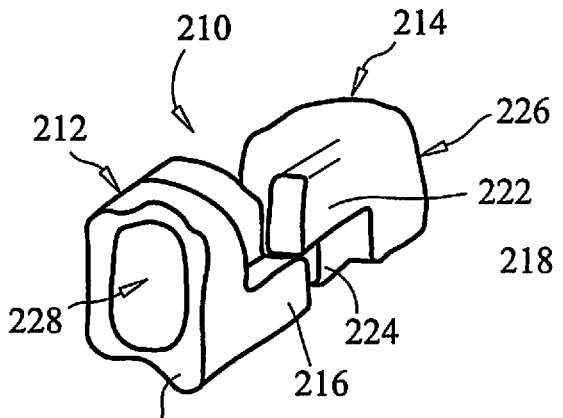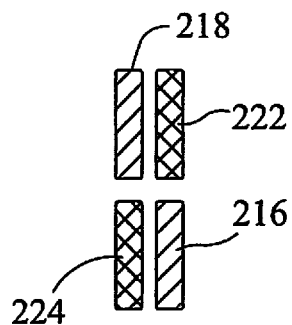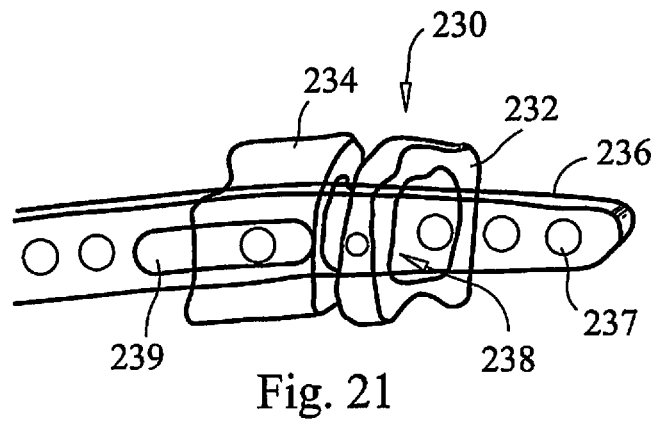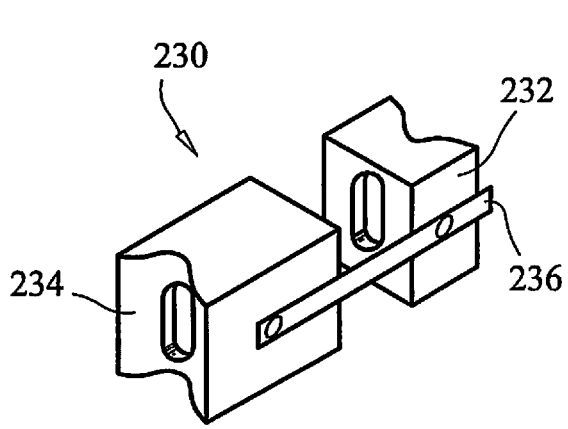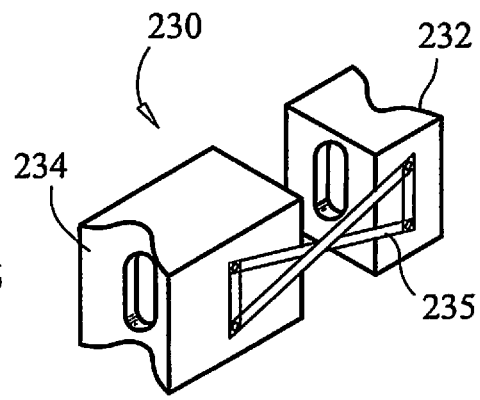

LAMINOPLASTY FIXATION DEVICES

CROSS-REFERENCE TO RELATED APPLICATIONS

This application is a divisional of U.S. application Ser. No. 11/936,334 filed Nov. 7, 2007, which claims priority to U.S. Provisional Application Ser. No. 60/864,731 filed on Nov. 7, 2006, the contents of which are incorporated herein by reference in their entireties for all purposes.

FIELD OF THE INVENTION

The present invention generally relates to devices and methods for treating degenerative conditions of the spine or for alleviating pain or discomfort associated with the spinal column. More specifically, the present invention is directed to laminoplasty fixation devices.

BACKGROUND OF THE INVENTION

In certain circumstances, the spinal canal extending through a patient's vertebrae is or becomes too narrow and constricts the spinal cord extending therethrough. Narrowing can be attributable to causes such as age, injury or removal of a spinal disk.

For instance, cervical spondylosis is a common degenerative condition of the cervical spine that most likely is caused by age-related changes in the intervertebral disks. As disk degeneration occurs, mechanical stresses result in osteophytic spurs, which may form along the interior aspect of the spinal canal and can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebra to slip with respect to each other, also compressing the spinal cord. Instability between vertebrae, such as caused by stretched and thickened ligaments can also produce pressure on the spinal cord and nerve roots.

Myelopathy, or affliction or injury of the spinal cord, occurs due to its compression. The rubbing of the spine against the cord can also contribute to this condition, and the spinal cord compression can ultimately compromise the blood vessels feeding the spinal core, further aggravating the myelopathy.

Traditional procedures for decompressing the spinal cord include a laminectomy, in which the lamina and spinal processes are removed to expose the dura covering the spinal cord. Another known procedure is a laminoplasty, in which the lamina is lifted off the dura, but not completely removed. According to one laminoplasty procedure sometimes referred to as an "open door" procedure, an osteotomy is performed in which a complete cut is made through one side of the vertebra, approximately between the lamina and lateral mass, while a partial-depth cut is made on the opposite lateral side. The lamina is then hinged open about the partial cut to increase the cross-sectional size of the spinal canal to decompress the spinal cord therein. In certain procedures, a laminoplasty plate is then fixed between the facet and the hinged open lamina. According to some known methods, the plate of an appropriate size is selected and bent to the desired shape and generally has a plurality of screw holes. In other known techniques, a strut of bone may be placed in the open portion within the lamina and the facet to help hold the open position of the lamina. In general, prior to the operation, the surgeon needs to measure the vertebra to determine the size of the plate necessary for implantation. At that point, a plate can be selected with the appropriate dimensions, and implanted at the site.

Improved laminoplasty fixation devices are needed. For example, a laminoplasty fixation device that may be varied in size prior to implantation is desirable so that a plate does not have to be custom selected and intensively shaped and formed prior to each surgery.

SUMMARY OF THE INVENTION

The present invention generally relates to laminoplasty fixation devices and methods of use. One embodiment of a vertebral implant constructed according to the invention comprises a first bone engaging portion configured for securing to a first cut portion of a vertebra and a second bone engaging portion configured for securing to a second cut portion of the vertebra. A body portion is provided for associating the first and second bone engaging portions at a preselected spacing from each other, wherein the implant is adjustable to select said spacing.

BRIEF DESCRIPTION OF THE DRAWINGS

The invention will be more readily understood with reference to the embodiments thereof illustrated in the attached figures, in which:

FIG. 13 is a side view of another embodiment of a laminoplasty fixation device shown in an implanted position on a portion of a vertebral body;

FIG. 13A is an exploded side view of the embodiment depicted in FIG. 13;

FIG. 14 is an exploded side and top view of an alternative to the embodiment depicted in FIG. 13;

FIG. 15 is an exploded side and top view of another embodiment of a laminoplasty fixation device;

FIG. 16 is a perspective view of the embodiment depicted in FIG. 15;

FIG. 19 is a perspective view of another embodiment of a laminoplasty fixation device according to the invention;

FIG. 20 is a cross-sectional view of the embodiment of FIG. 19;

FIG. 21 is a perspective view of another embodiment of a laminoplasty fixation device according to the invention;

FIG. 22 is a perspective view of another embodiment of a laminoplasty fixation device according to the invention;

FIG. 23 is a perspective view of another embodiment of a laminoplasty fixation device according to the invention;

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. The features of one embodiment may be employed with other embodiments as the skilled artisan would recognize, even if not explicitly stated herein. It is to be understood that each specific element includes all technical equivalents that operate in a similar manner to accomplish a similar purpose.

Referring to FIGS. 1-29, embodiments of devices or implants for use in a unilateral or "open door" laminoplasty procedure are shown. Generally, in an "open door" laminoplasty procedure, an osteotomy is performed in which a complete cut is made through one side of the vertebra, approximately between the lamina and lateral mass, while a partial-depth cut is made on the opposite lateral side. The lamina is then hinged open about the partial cut to enlarge the spinal canal.

Figure 1:
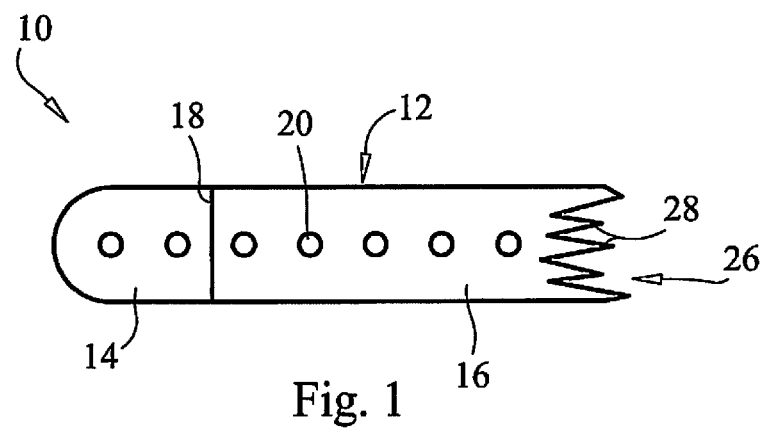
FIG. 1 is a top view of one embodiment of a laminoplasty fixation device according to the invention.
Figure 2:
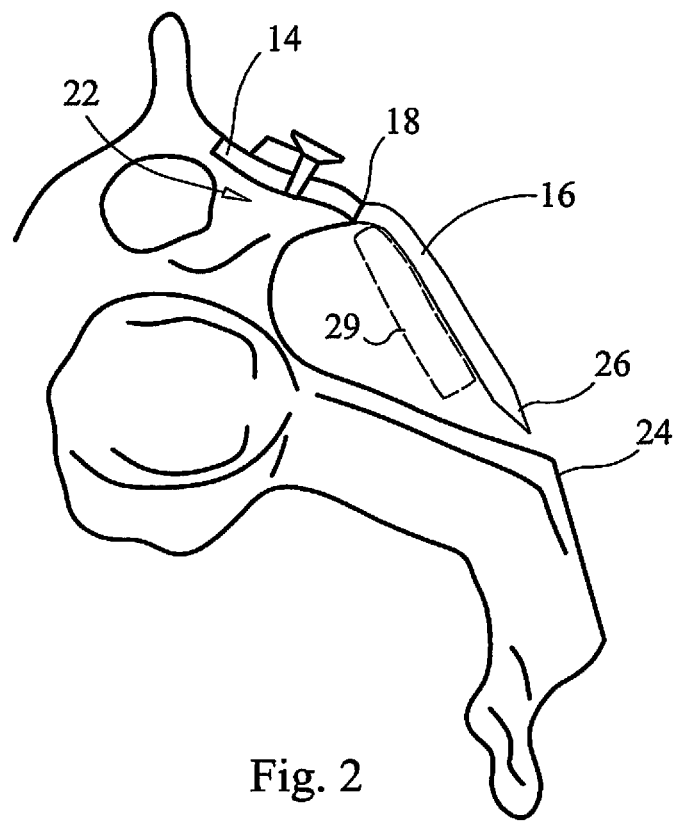
FIG. 2 is a side view of the embodiment of FIG. 1 shown in an implanted position on a portion of a vertebral body.

Referring to FIGS. 1 and 2 one exemplary embodiment of a laminoplasty fixation device 10 according to the invention is shown. In general, fixation device 10 comprises a unitary plate body 12 with a first portion 14 and a second portion 16 separated by a bendable section 18. Bendable section 18 generally comprises a thinner less rigid portion of plate body 12 configured allow second portion 16 to bend or rotate relative to first portion 14. Plate body 12 generally comprises a plurality of openings or holes 20 for receiving a bone fastener, such as a bone screw. The holes 20 may be disposed for accessing and inserting the fasteners from the outside of the bone to facilitate implantation. According to one embodiment, fixation device 10 is configured for use in an "open door" laminoplasty procedure with the first portion 14 generally configured for securing to a portion of a lamina 22 that has been cut and hinged away from the lateral mass 24. Second portion 16 of plate body 12 generally comprises a serrated or spiked free end 26. The spikes or serrations 28 at end 26 are configured to engage the lateral mass to prop the lamina open when the second portion 16 is rotated with respect to first portion 14. In one embodiment, plate 12 is made from a titanium material; however, in alternate embodiments any suitable implant material known to those skilled in the art may be used. In one embodiment a bone strut 29 may be attached to the inner surface of plate 12 to facilitate bone fusion or regeneration between the lateral mass and lamina. In alternate embodiments, plate 12 may comprise separate plate portions interconnected by a hinge member.

Figure 3:
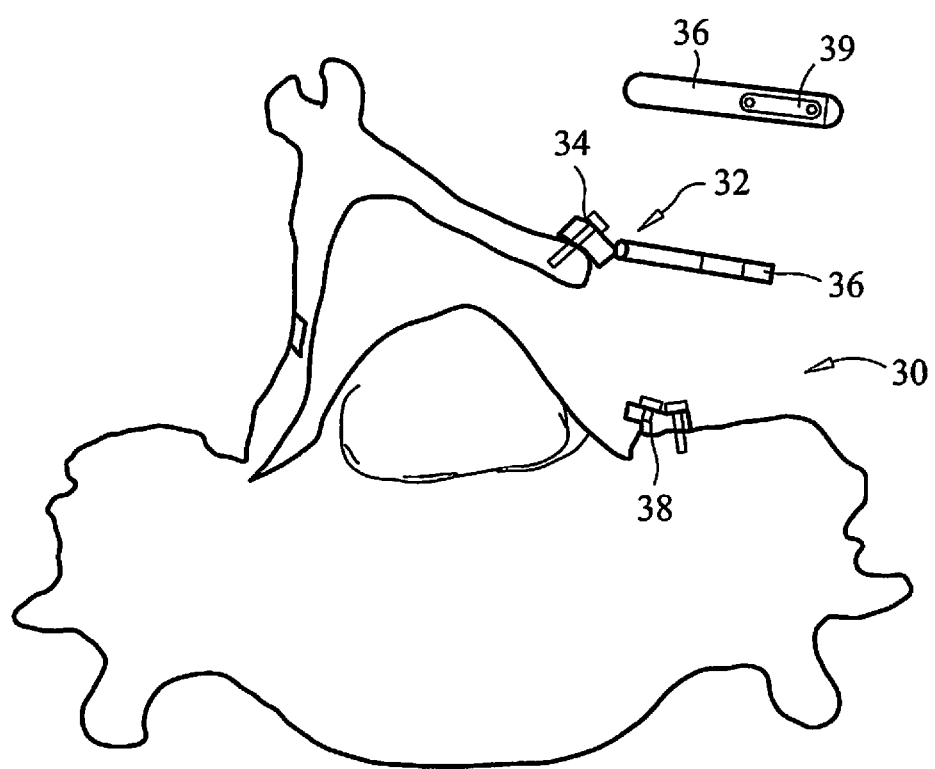
FIG. 3 is a side view of another embodiment of a laminoplasty fixation device shown in an implanted position on a portion of a vertebral body.

Referring to FIG. 3, another embodiment of a laminoplasty implant 30 is shown. Implant 30 generally comprises a swing plate body 32 with a first portion 34 rotatably connected to a second portion 36. Implant 30 is generally similar to plate 10 described above, except the integrated spikes 28 are replaced with a separate lateral mass anchor portion 38. In operation, first portion 34 and anchor portion 38 can be attached or fixed to the lamina prior to cutting through the lamina thereby facilitating an easier implantation procedure than attaching the first and anchor portions 34, 38 after cutting through the lamina. In one variation, plate body 32 comprises a slotted hole 39 to provide adjustability. Once the lamina is cut, the second portion of the plate may be swung into place and may be attached or fixed to anchor portion 38 with a fixation device, such as a screw. In alternate embodiments, a latch mechanism may be used to fixably connect second portion 36 to anchor portion 38.

Figure 4:
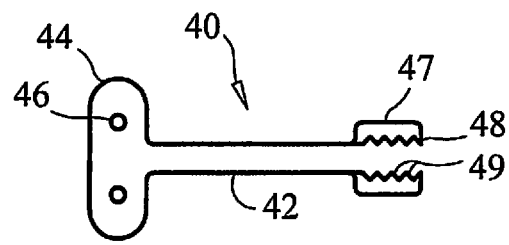
FIG. 4 is a side view of another embodiment of a laminoplasty fixation device according to the invention.

Referring to FIG. 4, another embodiment of a laminoplasty fixation device or implant 40 is shown. Implant 40 generally comprises an elongate body 42 with a first end portion 44 having one or more openings or holes 46 configured to receive fasteners and an opposite second end 47 comprising a bifurcated, yoked, or claw-like portion 48. Bifurcated portion 48 comprises bone engaging or locking features such as serrations, knurls, or teeth 49 positioned along the inner portion thereof. Claw 48 is configured to be deformable to compress teeth 49 against bone to fix plate body 42 to bone. According to one application of plate 42 for a laminoplasty, first end 44 may be attached to the lateral mass and second end 47 may be crimped to the lamina once it is cut and rotated or opened during the laminoplasty procedure. According to one embodiment, implant 40 may be made from titanium; however, in alternate embodiments any suitable biocompatible material may be used.

Figure 5:
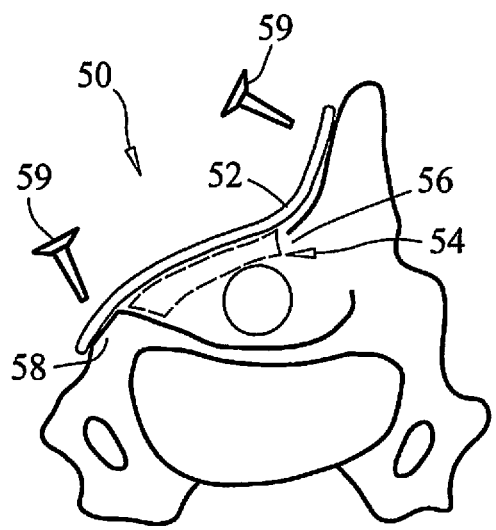
FIG. 5 is a side view of another embodiment of a laminoplasty fixation device shown in an implanted position on a portion of a vertebral body.
Figure 5A:
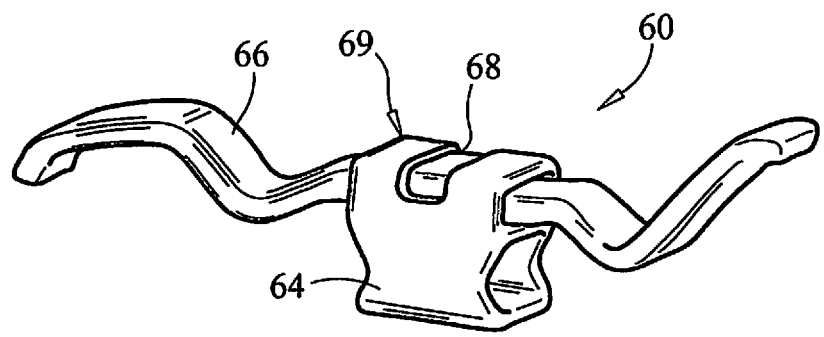
FIG. 5A is a perspective view of another embodiment of a laminoplasty fixation device according to the invention.

Referring to FIG. 5 another embodiment of a laminoplasty device or implant 50 constructed according to the invention is shown. Implant 50 generally comprises a flexible mesh body 52 that may be screwed or otherwise secured adjacent the lateral mass at one end and adjacent the lamina or spinous process at the opposite end. A rigid strut 54 may be attached to mesh body 52 for positioning between the lamina 56 and lateral mass 58. In one embodiment, mesh body 52 may be attached to bone at any location along its length by, for example, fasteners or screws 59. According to one embodiment, implant 50 may be made from a Dacron® or Gore-Tex® material. Referring to FIG. 5A, another embodiment of an implant 60 constructed according to the invention is shown. Implant 60, is similar to implant 50 except strut 64 is fixably slidably positionable along flexible strap 66. In one variation, strut 64 may comprise strap receiving members or slots 68 adjacent an upper sidewall 69 to slidingly accommodate strap 66 therethrough. In the embodiment of FIG. 5A, rigid strut 64 may be made from a PEEK material and may have a through-hole to permit bone growth and/or packing with bone or DBM material. The lateral ends of strut 64 may be indented or comprise a birdmouth-like profile to capture cut portions of the lateral mass and lamina and generally prevent movement of strut 64 in the posterior-anterior direction, i.e. into the spinal canal. Also, strap 66 generally prevents strut 64 from migrating. One advantageous feature of such a flexible mesh or strap body is that the implant may readily conform to the anatomy and it generally provides variability in placement of fasteners to secure the implant in place.

Figure 6:
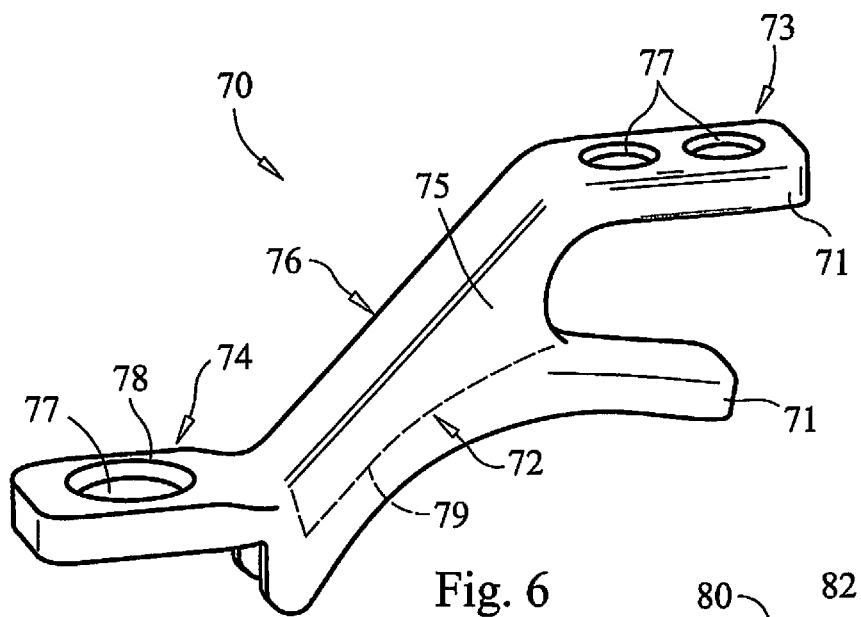
FIG. 6 is a perspective view of another embodiment of a laminoplasty fixation device according to the invention.

Referring to FIG. 6 another embodiment of a laminoplasty device or implant 70 constructed according to the invention is shown. Implant 70 generally comprises a unitary plate body 72 with a first portion 73 and a second portion 74 separated by an intermediate portion 75. Body 72 has a general "S" shape when viewed from the side, as shown in FIG. 6. When implant 70 is used in an "open door" laminoplasty procedure, the first portion 73 is generally configured for securing to a portion of a cut lamina and the second portion 74 is generally configured for securing to a portion of the lateral mass. In one embodiment, first portion 73 comprises a bifurcated or yoked end with spaced tines 71 configured and dimensioned to receive a portion of the lamina therebetween. According to one embodiment, intermediate portion 75 may have a hollow central region 76. The hollow region 76 may be packed with osteogenic material to facilitate fusion of the implant 70 with the patients cut bone portions. In addition, hollow region 76 allows access to cut bone portions after implantation and facilitates packing of osteogenic material therein. Also, a base wall may 79 be provided along the anterior side of hollow region 76 to prevent osteogenic material and bone growth from migrating into the spinal canal. In one variation, base wall 79 may be between about 1 mm and 2 mm thick. Plate body 72 generally comprises a plurality of openings or holes 77 for receiving a bone fastener, such as a bone screw. The holes 77 may be disposed for accessing and inserting the fasteners from the outside of the bone to facilitate implantation. In one embodiment, a countersink or scalloped region 78 may be provided adjacent openings or holes 77 to accommodate, among other things, a variable-angle screw to allow angulation of implant 70 with a fastener inserted therethrough.

Instead of a unitary or single plate body, laminoplasty fixation devices may comprise multiple components. For example, as shown in FIGS. 7-29, fixation devices generally comprise more than one component.

Figure 7:
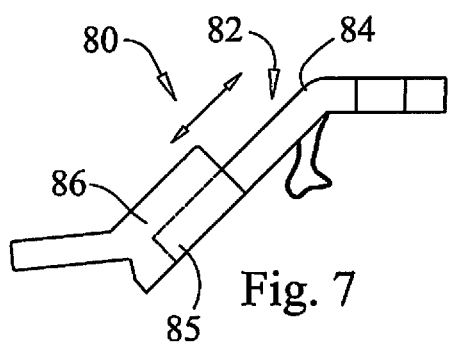
FIG. 7 is a side view of another embodiment of a laminoplasty fixation device according to the invention.

Referring to FIG. 7 another embodiment of a laminoplasty implant 80 according to the invention is shown. Implant 80 is similar to implant 70 shown in FIG. 6 and described above, except the implant body 82 comprises two separate components slidably connected together. According to one embodiment, first body portion 84 is slidably received within a receiving portion 85 of second body portion 86 with a dovetail fit. Such a sliding dovetail configuration facilitates distractability between the bone engaging end portions. As one skilled in the art may appreciate, such a feature is desirable for accommodating a variety of spacing between a lateral mass and lamina. According to one embodiment, the first and second body portions may be fixed relative to one another by a set screw or other know fixation device.

Figure 8:
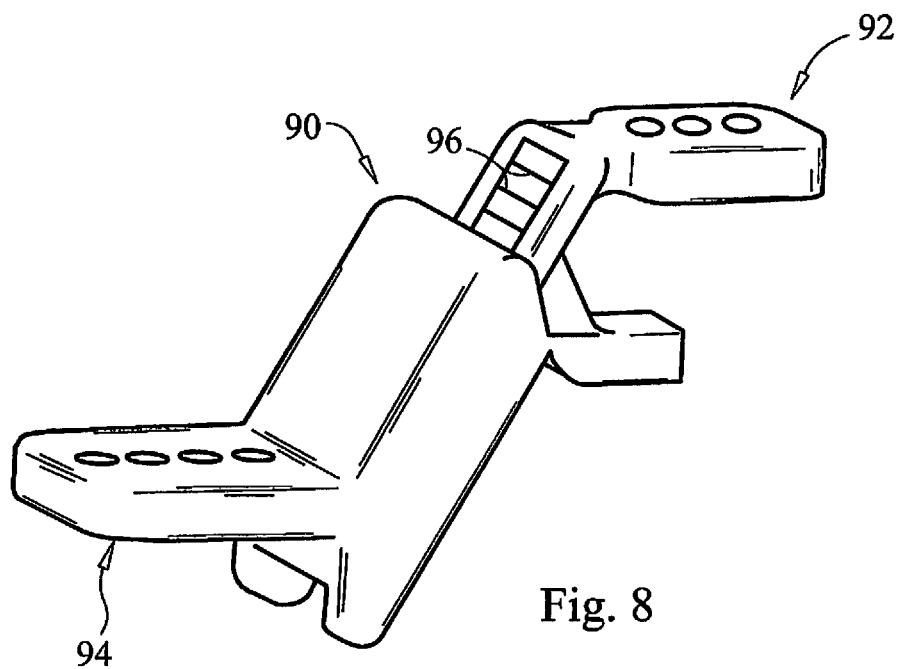
FIG. 8 is a perspective view of another embodiment of a laminoplasty fixation device according to the invention.

Referring to FIG. 8, another embodiment of a laminoplasty implant 90 according to the invention is shown. Implant 90 is similar to implant 80 described above with respect to FIG. 7 except the first and second body portions 92, 94 are adjustably connected by a ratchet mechanism. In one embodiment, first body portion has an upper surface comprising a plurality of ratchet features or teeth 96 that matingly interface with corresponding ratchet teeth (not shown) on the under surface of second body portion 94. In one embodiment, teeth 96 are unidirectional and first body portion 92 may be fixed with respect to second body portion 96 with a unidirectional or distraction movement. Such a ratchet interconnection promotes adjustability, since it is easy for a practitioner to increase the distraction or spacing of the device. For example, the first and second body portions may be immediately locked in position or fixed with respect to one another, thus eliminating the need for a set screw or other additional fixation device. In this regard, such an arrangement permits one step distraction and generally eliminates the need to use a trial insert to find a proper fit. As a result, a set of implants for use in surgery may have fewer parts. In addition, the distraction or relative movement between the first and second body portions is unidirectional which prevents recoil, retraction, bounce back, or backward movement during insertion.

Figure 9:
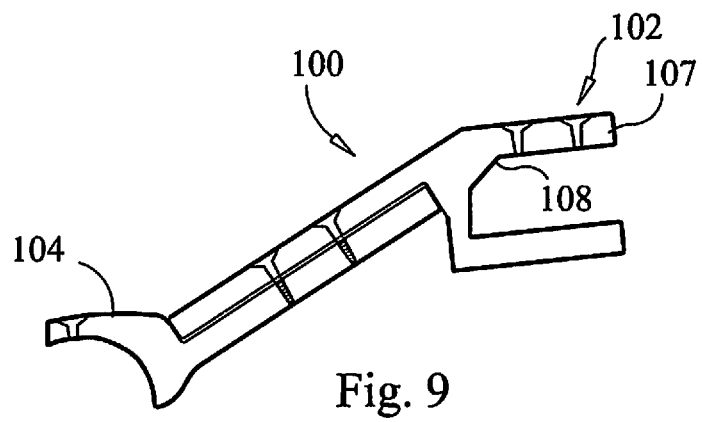
FIG. 9 is a side view of another embodiment of a laminoplasty fixation device according to the invention.
Figure 9A:
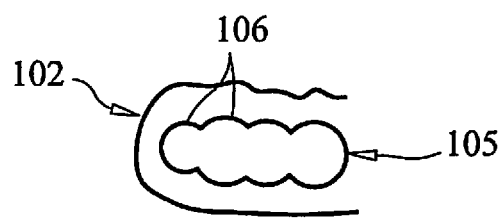
FIG. 9A is a partial top view of the embodiment of FIG. 9.
Figure 9B:
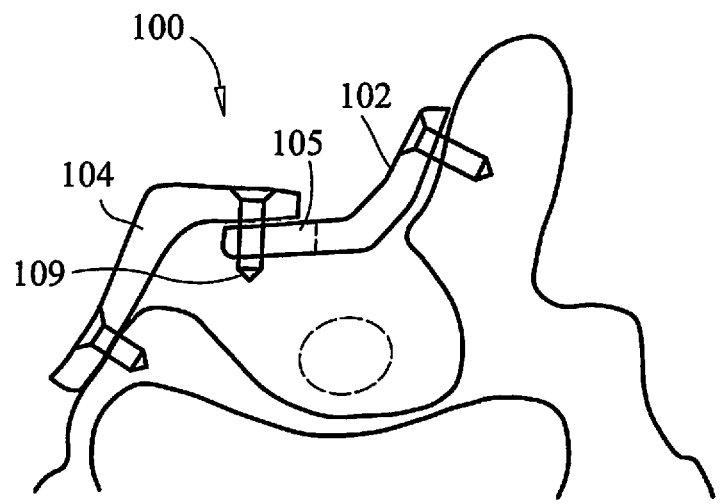
FIG. 9B is a side view of another embodiment of a laminoplasty fixation device shown in an implanted position on a portion of a vertebral body.

Referring to FIG. 9, another embodiment of a laminoplasty implant 100 according to the invention is shown. Implant 100 is similar to implants 80 and 90, described above, except that the first and second body portions 102, 104 are fixably adjustable with an elongate slot and screw connection. As best seen in FIG. 9A, an elongate slot 105 is configured to receive a fastener such as a screw therethrough. In one variation, one or more indentations or scalloped portions 106 are positioned about the perimeter of slot 105 to locate or position the fastener along the length of slot 105. According to one embodiment, first body portion 102 may be able to articulate with respect to bone engaging end portion 107. In this regard, bone engaging portion 107 may be attached to a lamina portion prior to bending or hinging of the lamina during the laminoplasty procedure. In one embodiment, a pivot pin 108 extends through first body portion 102 and bone engaging portion 107 to facilitate articulation. In an alternate embodiment, illustrated in FIG. 9B, first and second body portions 102, 104 may comprise unitary arched plate bodies with a slot 105 provided in one body portion for receiving a fastener 109 therethrough to facilitate fixable relative adjustment of the first and second body portions 102, 104.

Figure 10:
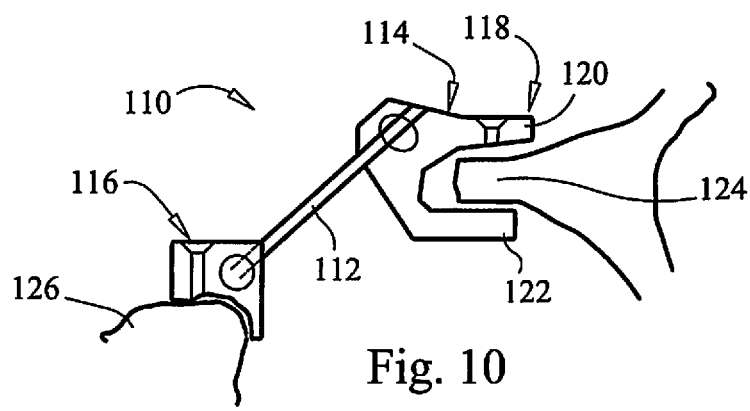
FIG. 10 is a side view of another embodiment of a laminoplasty fixation device shown in an implanted position on a portion of a vertebral body.

Referring to FIG. 10, another embodiment of a laminoplasty implant 110 according to the invention is shown. Implant 110 is similar to implants 80, 90 and 100 described above, except the intermediate body portion comprises an elongate rod 112 fixably adjustable between first and second bone engaging portions 114, 116. First and second bone engaging portions 114, 116 are configured to receive one or more fasteners to secure portions 114, 116 to bone. In one variation, shown in FIG. 10, first portion 114 comprises a yoke or forked end 118 with a top tine 120 and a bottom tine 122 and the tines 120, 122 are spacedly configured to engage opposite sides of a portion of bone, such as the lamina 124. According to one embodiment, rod 112 may be able to slide or move with respect to bone engaging portions 114, 116. Such a sliding configuration facilitates distractability between the bone engaging end portions. As one skilled in the art may appreciate, such a feature is desirable for accommodating a variety of spacing between a lateral mass and lamina. In addition, such a slidable rod configuration advantageously provides minimal canal encroachment while still allowing adjustable distraction. In another embodiment, one or both bone engaging portions 114, 116 may comprise a multi-axial screw and may allow screw angulation, such as adjacent the lateral mass 126.

Figure 11:
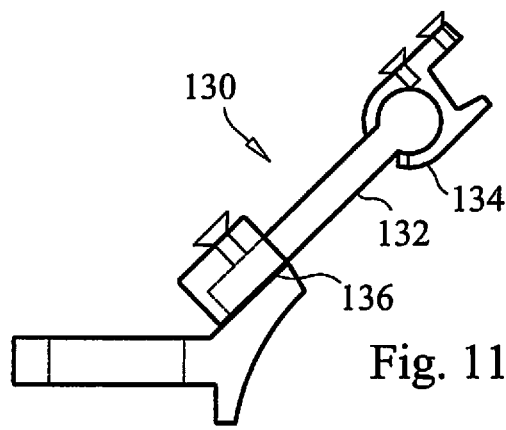
FIG. 11 is a side view of another embodiment of a laminoplasty fixation device.

Referring to FIG. 11, another embodiment of a laminoplasty implant 130 according to the invention is shown. Implant 130 is similar to implant 110 described above with respect to FIG. 10, except that the intermediate body portion or rod 132 is spherically connected to first bone engaging portion 134 and slidably connected to second bone engaging portion 136. In this regard, such a spherical connection facilitates distractability between the bone engaging end portions while also allowing the first bone engaging portion 134 to articulate or move with distraction.

Figure 12:
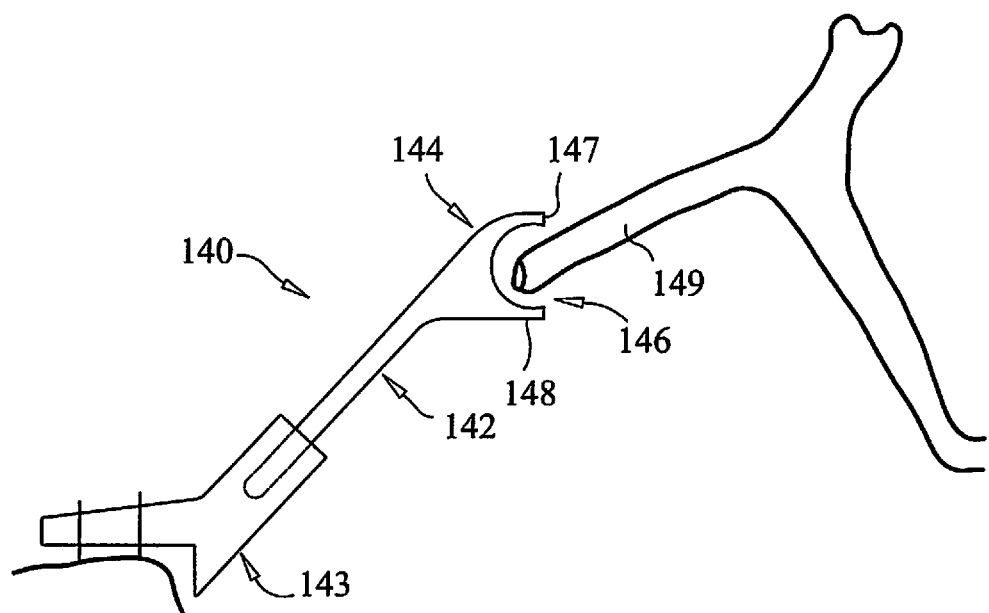
FIG. 12 is a side view of another embodiment of a laminoplasty fixation device shown in an implanted position on a portion of a vertebral body.

Referring to FIG. 12, another embodiment of a laminoplasty implant 140 according to the invention is shown. Implant 140 is similar to implant 130 described above, except that the first body portion 142 comprises an elongate body with an integrated first bone engaging portion 144. First bone engaging portion 144 comprises a yoke or forked end 146 with a top tine 147 and a bottom tine 148 and the tines 147, 148 are spacedly configured to engage opposite sides of a portion of bone, such as the lamina 149. According to one embodiment, first body portion 142 may be able to slide or move with respect to second bone engaging portion 145. Such a sliding configuration facilitates distractability between the bone engaging end portions. As one skilled in the art may appreciate, such a feature is desirable for accommodating a variety of spacing between a lateral mass and lamina.

Referring to FIGS. 13-14, another embodiment of a laminoplasty implant 150 according to the invention is shown. Implant 150 is similar to implant 110, described above with respect to FIG. 10 except that a first body portion comprises an elongate body 152 with an integrated first bone engaging portion 154 at distal end 156. First bone engaging portion 154 comprises a bottom hook portion 158 configured to engage opposite sides of a portion of bone, such as the lateral mass 159, as illustrated in FIG. 13. According to one embodiment, elongate body 152 may be able to slide or move with respect to second bone engaging portion 160. In one variation, elongate body 152 has a cylindrical cross-section and generally resembles a rod. In alternate embodiments, elongate member 152 may have a rectangular cross-section and generally resemble a bar. Second bone engaging portion 160 comprises a bottom hook portion 162 integrated with an upper receiving portion 164. Hook portion 162 is generally configured to engage opposite sides of a portion of bone, such as the lamina 165, as illustrated in FIG. 13. Receiving portion 164 is configured and dimensioned to fixably slidably receive a portion of elongate body 152. According to one embodiment, elongate body 152 may be fixed with respect to receiving portion 164 with a set screw 166. Such a fixable sliding configuration facilitates distractability between the bone engaging end portions. As one skilled in the art may appreciate, such a feature is desirable for accommodating a variety of spacing between a lateral mass and lamina.

Referring to FIGS. 15-16, another embodiment of a laminoplasty implant 170 according to the invention is shown. Implant 170 is similar to implant 150, described above with respect to FIGS. 13-14 except that a first body portion 172 comprises an elongate bar 174 with an upper ratchet portion comprising a plurality of ratchet features or teeth 176. According to one embodiment, bar 174 is integrated with a first bone engaging portion 178 at distal end 176 thereof. Bar 174 may be able to slide or move with respect to second bone engaging portion 180. Similar to the embodiment of FIGS. 13-14, first and second bone engaging portions 174, 180 generally comprise bottom hook portions 178, 182 configured to engage opposite sides of a portion of bone, such as the lateral mass and lamina, when implant 170 is installed. Second bone engaging portion 180 comprises an upper portion with a bar receiving portion 184 configured to slidably receive a portion of bar 172. According to this embodiment, receiving portion 184 generally comprises unidirectional teeth complimentary to ratchet teeth 176 of bar 172 and bar 172 may be fixed with respect to receiving portion 184 with a unidirectional ratchet mechanism. Such a ratchet interconnection facilitates easy adjustability. For example, the first and second bone engaging portions may be immediately locked in position or fixed with respect to one another, thus eliminating the need for a set screw or other additional fixation device. In this regard, such an arrangement permits one step distraction between the bone engaging portions 174, 180. In addition, the distraction or relative movement between the first and second bone engaging portions 174, 180 is unidirectional which prevents recoil, bounce back, or backward movement during insertion.

Figure 17:
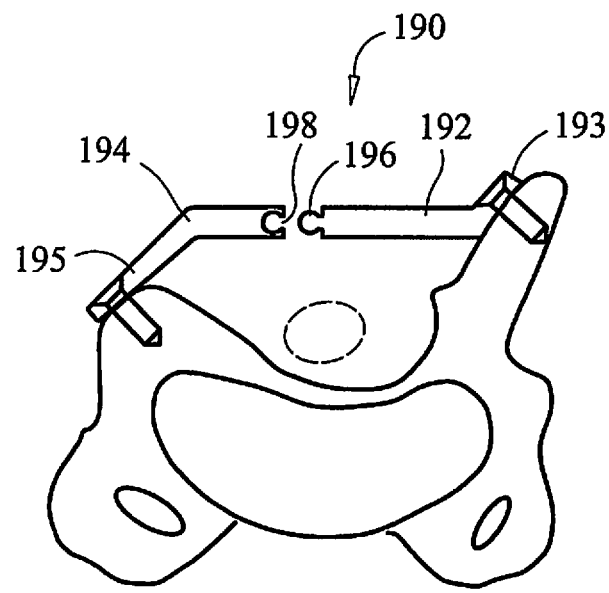
FIG. 17 is a side view of another embodiment of a laminoplasty fixation device shown in an implanted position on a portion of a vertebral body.

Referring to FIG. 17 another embodiment of a laminoplasty implant 190 according to the invention is shown. Implant 190 is similar to implant 100 shown in FIG. 9B described above, except the first and second body portions 192, 194 are linkable together by a ball-and-socket connection. According to one embodiment, first body portion 192 comprises a ball shaped end 196 configured and dimensioned to be received within a correspondingly shaped female or socket end 198 of second body portion 194. Such a ball-and-socket configuration facilitates angulation or hinging between the bone engaging end portions 193, 195. As one skilled in the art may appreciate, such a feature is desirable for accommodating a variety of spacing between a lateral mass and lamina. In alternative embodiments, different types of linkages may be utilized. For example, in one variation a puzzle piece type connection may be used. In another embodiment a dovetail type linkage connection may be utilized. According to these various embodiments, one skilled in the art may appreciate that such removably linkable connections may facilitate insertion of first and second body portions individually.

Figure 18:
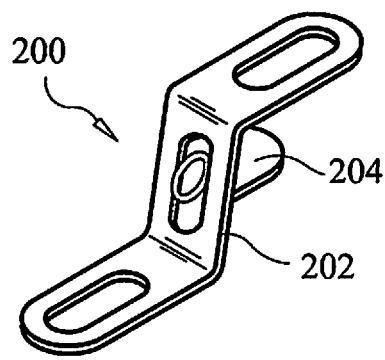
FIG. 18 is a perspective view of another embodiment of a laminoplasty fixation device according to the invention.
Figure 18A:
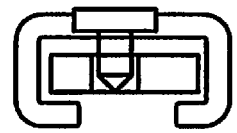
FIG. 18A is a cross-sectional view of the embodiment of FIG. 18.
Figure 18B:
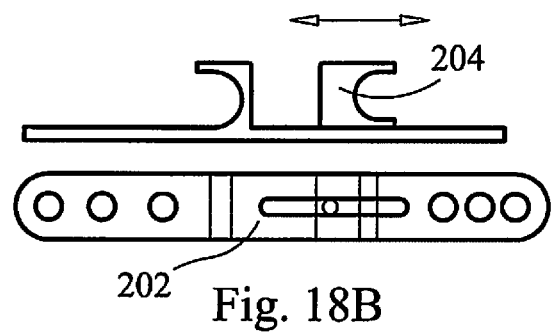
FIG. 18B is a top and side view of another embodiment of a laminoplasty fixation device according to the invention.

Referring to FIGS. 18 and 18A, another embodiment of a laminoplasty implant 200 according to the invention is shown. Implant 200 is similar to implant 80 shown in FIG. 7 described above; except the implant body 202 comprises a strut 204 fixably slidable with respect to body portion 202. According to one embodiment, strut 204 may be slidably received within body portion 202 with a slotted fit, as best seen in FIG. 18A. Such a sliding configuration facilitates distraction along the length of body portion 202. According to one embodiment, the strut 204 may be fixed relative to body portion 202 by a set screw or other know fixation device. Referring to FIG. 18B an alternate embodiment of an implant with an adjustable strut member is shown.

Referring to FIGS. 19-20 another embodiment of a laminoplasty implant according to the invention is shown. Implant 210 comprises two separate components slidably connected together. According to one embodiment, first body portion 212 is slidably received within second body portion 214 with an offset finger fit. First body portion 212 generally comprises first and second finger portions 216, 218 extending longitudinally from opposite corner sections of a first bone engaging end 220. Second body portion 214 generally comprises third and fourth finger portions 222, 224 extend longitudinally from opposite corner sections of a second bone engaging end 226. As seen in FIG. 19, first and second finger portions 216, 218 of first body portion 212 are configured and dimensioned to meshingly longitudinally engage and fixably slide with respect to third and fourth finger portions 222, 224 of second body portion 214. As shown in FIG. 20, first and second finger portions 216, 218 are configured may be angularly offset with respect to third and fourth finger portions 222, 224 to facilitate uni-axial sliding of first body portion 212 with respect to second body portion 214 and prevent torsion or twisting. Such a sliding configuration facilitates distractability between the bone engaging end portions. As one skilled in the art may appreciate, such a feature is desirable for accommodating a variety of spacing between a lateral mass and lamina. According to one embodiment, the first and second body portions may be fixed relative to one another by a set screw or other know fixation device. Referring to FIG. 19, in one embodiment first and second body portions 212, 214 may have a hollow central region 228. The hollow region 228 may be packed with osteogenic material to facilitate fusion of the implant 210 with cut bone segments.

Referring to FIG. 21, another embodiment of a laminoplasty implant 230 according to the invention is shown. Implant 230 comprises two bone engaging strut members 232, 234 disposed along a track plate 236. Struts 232, 234 generally comprise bone engaging portions configured to engage opposite sides of a portion of bone, such as the lamina and lateral mass in a laminoplasty procedure. According to one embodiment, track 236 is slidably received within hollow central portion 238 of strut members 232, 234 and strut members may generally be positioned anywhere along the length of track 236 as desired by a practitioner. In this regard, one ore more holes 237 or slots 239 may be provided along the length of track 236 for receiving a fastener therethrough to fix struts 232, 234 in place along the length of track 236. Such a fixable sliding configuration facilitates distractability between the struts 232, 234. As one skilled in the art may appreciate, such a feature is desirable for accommodating a variety of spacing between a lateral mass and lamina. Referring to FIG. 22, in an alternate embodiment, strut members 232, 234 may be fixably slidably disposed along a lateral side of a track plate 236. In another embodiment, shown in FIG. 23, strut members 232, 234 may be positioned adjacent a scissor bar expansion mechanism 235 to facilitate fixable variable spacing of strut members 232, 234.

Figure 24:
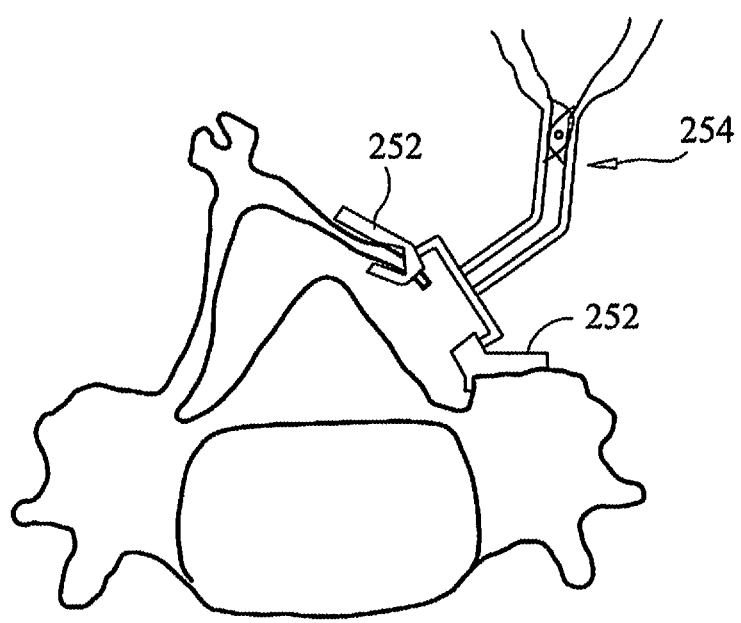
FIG. 24 is a side view of another embodiment of a laminoplasty fixation device shown in an implanted position on a portion of a vertebral body.
Figure 25:
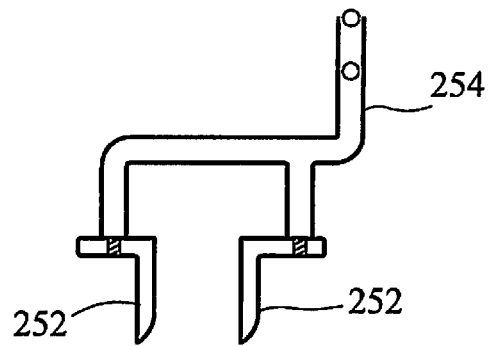
FIGS. 25-29 are a side views installation steps for implanting the laminoplasty fixation device of FIG. 24.
Figure 26:
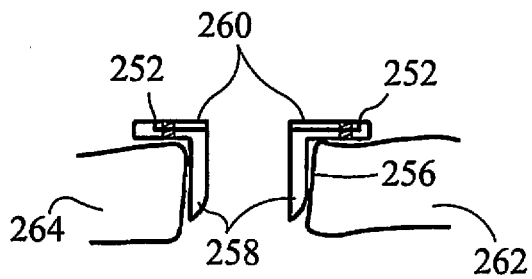
Figure 27:
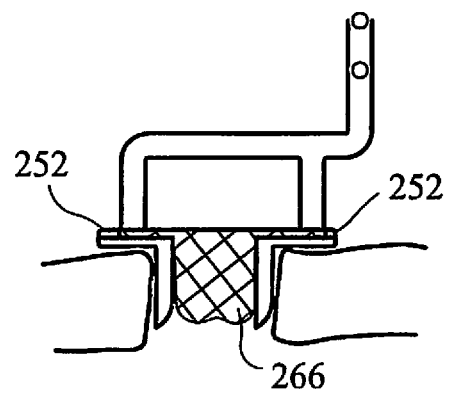
Figure 28:
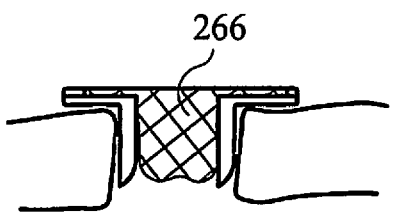
Figure 29:
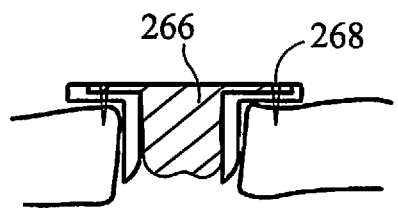

Referring to FIGS. 24-29, another embodiment of a laminoplasty implant 250 and installation method is shown. In this embodiment end plates 252 are inserted between cut bone segments with a distractor tool 254 to facilitate distraction, as best seen in FIG. 24. Plates 252 generally comprise an "L" shaped body 256 with a bone cover arm portion 258 extending distally from an elongate upper surface 260. According to one embodiment, plates 252 are configured and dimensioned to be attached to a distractor tool 254, as illustrated in FIGS. 24-25, to facilitate insertion between bone segments. Once the plate tips 252 are inserted between bone segments and sufficient distraction is achieved, plates 252 may be detached from distractor 254 and left in place against opposing portions 262, 264 of the spaced bone segments. Referring to FIG. 27, in one embodiment, a spacer insert 266 may then be inserted between end plates 252 to maintain the spacing between the bone segments and facilitate bony fusion. In one variation, spacer 266 may slide into place between arm portions 258 by a mating fit, such as a dovetail fit, to prevent movement of spacer 266 in a lateral or torsional direction. Spacer 266 may be various sizes and shapes as desired by a practitioner depending on the indication. As shown in FIG. 29, once installed between end plates 252, spacer 266 may fixed in place with respect to the bone segments and endplates with a fastener 268, such as a screw. According to one variation, endplates 252 and spacer 266 may be made from titanium.

Figure 30:
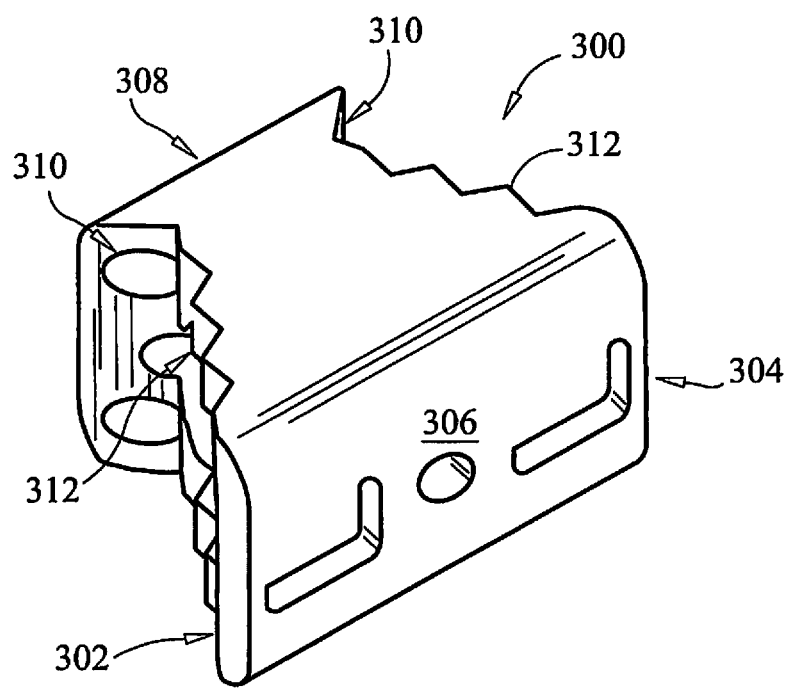
FIG. 30 is a perspective view of another embodiment of a laminoplasty fixation device according to the invention.
Figure 31:
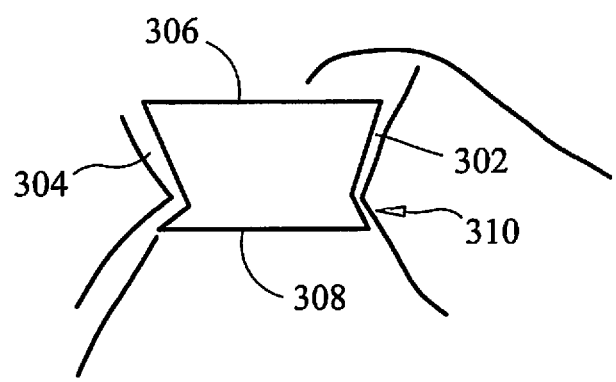
FIG. 31 is a side view of the embodiment of FIG. 30 shown in an implanted position on a portion of a vertebral body.

Referring to FIGS. 30-31, an embodiment of an implant for use in a bilateral or "french door" laminoplasty procedure is shown. In a "french door" laminoplasty procedure, the spinous process of a targeted vertebra is bisected along the saggital plane and the segments are separated to enlarge the spinal canal.

FIGS. 30 and 31 are perspective and side views of another embodiment of an implant 300 according to the invention. Implant 300 comprises a general trapezoidal peripheral shape when viewed from the side with bone engaging end walls 302, 304 extending angularly inward from posterior wall 306 toward anterior wall 308. In one variation anterior wall 308 is shorter in length than posterior wall 306, thus forming a general wedge-like profile. A bird-mouth, shelf, or lip 310 may be provided along end walls 302, 304. In one embodiment, lip 310 is positioned closer to anterior wall 308 than posterior wall 306, such that end walls 302, 304 widen laterally outward from the lip toward anterior wall 308. In this regard, such a bird-mouth or lip 310 facilitates secure engagement with an anterior portion of the bisected spinous process and generally prevents movement of implant 300 in the posterior direction when the implant is installed. In one variation, end walls 302, 304 of implant 300 may comprises serrations or ridges 312 to facilitate engagement or purchase with bone. In one embodiment, implant 300 may comprise a hollow central portion 314 to accommodate packing of osteogenic material therein, promote bone growth therethrough, and facilitate bone fusion. One or more through holes 316 may be provided to facilitate attachment via suture and/or bone fastener. In one embodiment, implant 300 may be made from a made of a polyether-ether-ketone (PEEK) plastic material; however any known biocompatible material may be used. Several known advantages of PEEK plastic material include that it is radiolucent and may be more easily sterilized than other plastics in addition to providing proven bio-compatibility with a modulus of elasticity approximating that of bone.

While the invention herein disclosed has been described by means of specific embodiments and applications thereof, numerous modifications and variations can be made thereto by those skilled in the art without departing from the scope of the invention.

What is claimed is:
1. A vertebral implant, comprising:
 a first bone engaging portion having an upper and lower surface configured for securing to a first cut portion of a vertebra; and a second bone engaging portion having an upper and lower surface configured for securing to a second cut portion of the vertebra;

wherein one of the first and second bone engaging portions includes a connecting body portion having an upper surface, a lower surface, and an opening for receiving the other of the first and second bone engaging portions, wherein the connecting body portion comprises a central longitudinal axis extending along its length and the first and second bone engaging portions are angled relative to the central longitudinal axis, wherein the first bone engaging portion extends away from the lower surface of the connecting body in a first direction and the second bone engaging portion extends away from the upper surface of the connecting body in a second direction opposite to the first direction, and wherein the connecting body portion and the first or second bone engaging portion interconnect with a dovetail fit.

2. The vertebral implant of claim 1, wherein the implant is a laminoplasty implant, the first and second vertebral portions being first and second portions enclosing the spinal canal of the vertebra.

3. The vertebral implant of claim 2, wherein the first vertebral portion comprises a lateral mass or a portion of the lamina of the vertebra, and the second vertebral portion comprises at least a portion of the lamina.

4. The vertebral implant of claim 1, wherein the first bone engaging portion is in fixed association with the connecting body portion.

5. The vertebral implant of claim 1, wherein the first and second bone engaging portions are capable of being secured to the first and second cut portions, respectively, and the connecting body portion is in fixing association with the first and second bone engaging portions to fix the distance therebetween.

6. The vertebral implant of claim 1, wherein the connecting body portion is slidable with respect to the first bone engaging portion along the longitudinal axis.

7. The vertebral implant of claim 1, wherein the first bone engaging portion includes an attachment portion having at least one opening for receiving a bone fastener and an extension portion, and the attachment portion is angled relative to the extension portion.

8. The vertebral implant of claim 1, wherein the second bone engaging portion includes an attachment portion having at least one opening for receiving a bone fastener, and the attachment portion is angled relative to the connecting body portion.

9. The vertebral implant of claim 1, wherein the vertebral implant has a general S-shape when viewed from the side.

10. A vertebral implant, comprising:
a first bone engaging portion configured for securing to a first cut portion of a vertebra;
a second bone engaging portion configured for securing to a second cut portion of the vertebra; and
a connecting member having an upper surface and a lower surface, and configured for associating the first and second bone engaging portions at a preselected spacing from each other;
wherein the connecting member comprises a central longitudinal axis extending along its length and the first and second bone engaging portions are angled relative to the central longitudinal axis, wherein the first bone engaging portion extends away from the lower surface of the connecting body in a first direction and the second bone engaging portion extends away from the upper surface of the connecting member in a second direction opposite to the first direction, and
wherein the connecting member and the first or second bone engaging portion interconnect in a dovetail.

11. The vertebral implant of claim 10, wherein the implant is a laminoplasty implant, the first and second vertebral portions being first and second portions enclosing the spinal canal of the vertebra.

12. The vertebral implant of claim 11, wherein the first vertebral portion comprises a lateral mass or a portion of the lamina of the vertebra, and the second vertebral portion comprises at least a portion of the lamina.

13. The vertebral implant of claim 10, wherein the first and second bone engaging portions are capable of being secured to the first and second cut portions, respectively, and the connecting member is in fixing association with the first and second bone engaging portions to fix the distance therebetween.

14. The vertebral implant of claim 10, wherein the connecting member is slidable with respect to the second bone engaging portion along the longitudinal axis and the connecting element is substantially constrained from movement with respect to the second bone engaging portion in all other directions.

15. The vertebral implant of claim 10, wherein the first bone engaging portion includes an attachment portion having at least one opening for receiving a bone fastener and an extension portion, and the attachment portion is angled relative to the extension portion.

16. The vertebral implant of claim 10, wherein the second bone engaging portion includes an attachment portion having at least one opening for receiving a bone fastener, and the attachment portion is angled relative to the connecting body portion.

17. The vertebral implant of claim 10, wherein the vertebral implant has a general S-shape when viewed from the side.

* * * * *